(12) United States Patent
Viller

(10) Patent No.: US 8,292,942 B2
(45) Date of Patent: Oct. 23, 2012

(54) DOUBLE-BALLOON DELIVERY SYSTEM FOR AN IMPLANTABLE ECCENTRIC STENT

(76) Inventor: Alexander G. Viller, Moscow (RU)

( * ) Notice: Subject to any disclaimer, the term of this patent is extended or adjusted under 35 U.S.C. 154(b) by 532 days.

(21) Appl. No.: 12/550,435

(22) Filed: Aug. 31, 2009

(65) Prior Publication Data

US 2010/0070014 A1    Mar. 18, 2010

Related U.S. Application Data

(63) Continuation-in-part of application No. PCT/RU2008/000590, filed on Sep. 12, 2008.

(51) Int. Cl.
*A61F 2/06* (2006.01)
(52) U.S. Cl. .............. 623/1.11; 623/1.15; 623/1.18; 623/1.34; 623/1.37; 623/1.42; 604/101.05; 604/103.07
(58) Field of Classification Search ............ 604/103.07, 604/916, 919; 623/1.1
See application file for complete search history.

(56) References Cited

U.S. PATENT DOCUMENTS

| 4,571,240 | A | 2/1986 | Samson et al. | |
|---|---|---|---|---|
| 7,252,679 | B2 | 8/2007 | Fischell | |
| 2005/0137621 | A1* | 6/2005 | Stahl et al. | 606/194 |
| 2007/0142900 | A1* | 6/2007 | Balaji | 623/1.16 |
| 2007/0225677 | A1* | 9/2007 | Rowe et al. | 604/509 |
| 2008/0177370 | A1* | 7/2008 | Stys | 623/1.15 |

FOREIGN PATENT DOCUMENTS

| WO | WO 2005/046523 A1 | 5/2005 |
|---|---|---|
| WO | WO 2010/030204 A1 | 3/2010 |

* cited by examiner

*Primary Examiner* — Bruce E Snow
*Assistant Examiner* — Brian Dukert
(74) *Attorney, Agent, or Firm* — Bardmesser Law Group

(57) ABSTRACT

A system for delivery of a stent dilatable by means of a balloon, including a multilumen polymeric catheter having at least two balloons at the input end, where the distal balloon can expand an eccentric stent mounted on it, and the proximal balloon of smaller diameter has, at least, two radiopaque labels (markers) and has a capability of accurate orientation of the stent in an artery lumen.

14 Claims, 4 Drawing Sheets

1.1  1.2  1.3

2.1  2.2  2.3

5.1

5.2

5.3

DOUBLE-BALLOON DELIVERY SYSTEM FOR AN IMPLANTABLE ECCENTRIC STENT

CROSS REFERENCE TO RELATED APPLICATIONS

This application is a continuation-in-part of PCT/RU2008/000590, filed 12 Sep. 2008, which is incorporated herein by reference in its entirety.

BACKGROUND OF THE INVENTION

The invention relates to medical appliances, namely, to devices used in endovascular surgery and intervention cardiology for restoration of narrowed bifurcation sites of a lumen of blood vessels, and also for treatment of an artery in the presence of an unstable atherosclerotic plaque for prevention of its rupture and an acute artherothrombosis, which is a basic etiological factor of an acute myocardial infarction.

At present, modern diagnostic methods (computer tomography, intravascular ultrasonic research, intravascular ultrasound imaging), allow accurate visualization of an unstable plaque in a lumen of a coronal artery. The latter, irrespective of degree of an obturation of an arterial lumen, is the basic morphological substrate for development of an acute myocardial infarction. Eccentricity of an unstable plaque dictates its necessity for selective stenting, especially in case of hemodynamically insignificant stenosis.

Delivery of instruments or a pharmaceutical composition directly to a place of damage in a vessel by means of conduction catheters is generally applied in the practice of endovascular surgeries, including in intervention cardiology. Upon placing a conduction catheter in an orifice of a coronary artery or some other artery, a coronary conductor is moved into a lumen of a blood vessel to enable advancing various instruments (balloon catheters, stents). The stent delivery systems of delivery of stents in use today and the stents themselves have a standard configuration in the shape of a monorail (over-the-wire) balloon catheter with a cylindrical stent mounted on a dilated balloon. After stent positioning in the narrowed vascular segment, pressure is increased in a balloon catheter, thus forcing expansion of both the catheter, and the stent mounted on it. Thus, the normal diameter of an artery is restored.

At the same time, there is a problem of restoration of a normal lumen of arteries in a zone of their bifurcation. At present, such operations, as a rule, require use of two guiding wires (sometimes referred to as "conductors") which are moved into the main blood vessel and a lateral branch, thus enabling simultaneous insertion of instruments into the blood vessels and performance of "kissing balloon dilatation".

There is also a problem of accurate orientation of instruments or devices inserted by means of a guiding catheter. Such a problem, in particular, is very acute in the practice of arterial stenting. Stenting arteries in a zone of bifurcation, especially the coronary arteries, constitute one of the main problems in interventional cardiology. As such, the most difficult is the operation of stenting arteries close to a lateral branch (blood vessel). At present, the techniques of stenting are widely used in cases where the stent is implanted into the main artery, the wire is introduced in a lateral branch through a cell of the stent and definitive angiographic result of operation is generated after the balloon angioplasty of the bifurcation zone by two "kissing" balloons. The procedure of stenting bifurcation lesions of arteries is also carried out by two stents simultaneously (techniques: cullotte, crush, V-stenting, T-stenting), and is accompanied by the increased risk of damage of an arterial wall, high risk of restenosis and intra-operative technical difficulties.

The problem of complete optimization of the artery diameter in the bifurcation zone is a difficult problem if conventional stents are used. There are several types of special bifurcation stents (for example Frontier stent (Abbot Vascular Inc.)) where the technical result is achieved by application of two balloons and two conductors to which the stent is mounted and which are positioned both in the main artery and in a lateral branch.

Another group of bifurcation stents has a special mesh structure that has an aperture for the lateral branch (SLK-View™ stent, Stentys), that allows optimizing implantation of the second stent in the lateral branch. Also, the nitinol bifurcation stent AXXESS Plus, from Devax Inc., has certain clinical applications, and which has the shape of a truncated cone, thus, the basic advantage of this stent at stenting the main artery consists in lower probability of atheromatosis mass shift in the lateral branch. At the same time, all bifurcation stents used in the current clinical practice have a design which, to certain extent, provides for successful main artery stenting and reinforcing the orifice of a lateral branch, but coverage throughout a sufficient length of the lateral branch is not provided. The specialized stents have, as a rule, a complex design comprising two balloons, two conductors (guide wires) and a limited range of application.

Russian Federation patent No. 192810 describes a kit for transluminal introduction of a tubular stent, including a self-dilatable tubular stent representing a transplant and the device for introduction of the stent, is known. This kit does not solve the problem of the high-precision placement of the stent in an orifice of a lateral arterial branch.

Also known is an eccentric stent, dilatable (expandable) by means of a balloon catheter, for implantation in a lateral arterial branch (see the U.S. Patent Publication No. 2004/0186560). The design of this stent is adapted for implantation in the orifice segment of a lateral branch of a coronary artery. However, the system of radiopaque labels used in this design does not provide for accurate enough positioning of the truncated part of a stent in the orifice segment of an artery, which can essentially influence safety endovascular operations.

The most similar to the claimed invention is the technical solution described in U.S. Pat. No. 7,252,679. This technical solution describes a stent comprising: a thin-walled, multi-cellular, tubular structure with a length and having in the unexpanded and unbent position a longitudinal axis passing through the center of the stent; a proximal end and a distal end; a multiplicity of circumferential sets of strut members, longitudinally separated each from the other and each set of strut members forming a closed, cylindrical portion of the stent; the stent also having a proximal set of circumferentially arranged strut members located at the proximal end of the stent and the proximal set of strut members oriented in a first plane generally transverse to the longitudinal axis; a distal set of circumferentially arranged strut members located at the distal end of the stent and the distal set of strut members oriented in a second plane generally transverse to the longitudinal axis; and a plurality of central sets of circumferentially arranged strut members positioned between the proximal and distal sets of strut members each of said central sets of circumferentially arranged stent members oriented in the same direction, and the central sets of strut members meeting the proximal set of strut members along a third plane; the first plane of the most proximal set of strut members having an angulation between 15 and 75 degrees with respect to the longitudinal axis of the stent when the stent has been expanded within a vessel of the human body, and the first, second and third planes intersecting with one another. The stent is self-expandable and is mounted on a rapid exchange stent delivery catheter. For better navigation, the stent is provided with a radiopaque marker attached either to the most proximal or to most distal location on the most proximal set of strut members.

While the design of the deliverable part of the stent has certain merits, the navigation system represented by a sole radiopaque marker, offers limited help to a clinician as the position of the marker is described by one coordinate only.

SUMMARY OF THE INVENTION

The problem to be solved by the claimed invention, consists in developing a design of a system for endovascular delivery of instruments, devices and/or medicinal substances, which would allow reliable fixation of a working part of the system in a blood vessel and, at the same time, would ensure high-precision orientation of the working part of the system and, accordingly, instruments and devices (in an example described further, such a device is represented by a stent) delivered by means of such system.

The above problem is solved by creation of an advanced design of the delivery system consisting of a multilumen polymeric catheter, of which the distal end (the part entering a blood vessel) is equipped with two polymeric balloons arranged in-line, the distal one for expansion of an eccentric stent mounted on it, and the proximal one, having smaller diameter, supplied with radiopaque labels (markers), for exact 3D positioning of the stent in an arterial lumen under fluoroscopy control.

For normal functioning of the claimed delivery system, it is important that at least one lumen of the polymeric catheter has a capability of being used for insertion of a guiding conductor, and at least one more lumen has a of being used for expansion of the balloons, mainly, by means of radiopaque substance.

For normal functioning of the claimed delivery system it is preferable that the lumen in the polymeric catheter, intended for introduction of the guiding conductor, is formed hollow throughout the entire body of the catheter.

As an acceptable alternative, it is possible to use a polymeric catheter with a lumen for a guiding conductor, extending through the distal part only.

For normal functioning of the delivery system it is important that the stent dilatable by means of a balloon has been formed as an eccentric, namely, in the shape of a cylinder truncated at both ends, where the angle between the longitudinal axis of the stent and the section plane is within the range of 30 to 70 degrees.

Alternatively, it is also acceptable that the eccentric stent dilatable by means of a balloon is formed in the shape of a cylinder truncated at one end only; where the angle between the longitudinal axis of the stent and the section plane is within the range of 15 to 80 degrees, preferably 30 to 70 degrees.

The stent should preferably be made of biologically neutral materials, for example, of steel types 316L, CoCr, CoNi, nitinol, gold, platinum.

Alternatively, the stent can be made of a biodegradable (biosoluble) material, whose structure should include, in some cases, a pharmaceutical substance or cells.

Additionally, the pharmaceutical substance or cells can be placed on the stent directly, and also can be included in structure of the polymeric coating layer covering the stent either entirely or partially. Two balloons forming a part of the delivery system have different diameters, where the proximal balloon has a smaller diameter. Its length is not strictly determined; nevertheless, for the system's flexibility it is preferable to have the length of the proximal balloon shorter than that of the distal balloon. Exemplary distal balloon length is about 8-40 mm, and exemplary proximal balloon length is about 2-15 mm.

The design of the delivery system ensures exact positioning of the truncated stent in a lumen of an artery due to presence of a small balloon (hereinafter referred to as a "signal balloon") located more proximally of the balloon carrying the mounted stent.

The signal balloon is supplied with at least two radiopaque labels differing not only in their location, but also in their sizes. In the example presented hereafter, the smaller label corresponds to the short side of the truncated stent, and the larger label corresponds to the longer side of the truncated stent.

In the exemplary embodiment, the proximal and the distal balloons are connected with the same lumen of the polymeric catheter; nevertheless, it is possible that they be connected with different lumens of the polymeric catheter.

Both the proximal and the distal balloons are extendable at the impact of a contrast agent pumped into their cavities through the lumens of the polymeric catheter.

BRIEF DESCRIPTION OF THE DRAWINGS

For better understanding of the invention, the description of the structure and functioning of the delivery system follows with reference to corresponding drawings.

Figure 1:
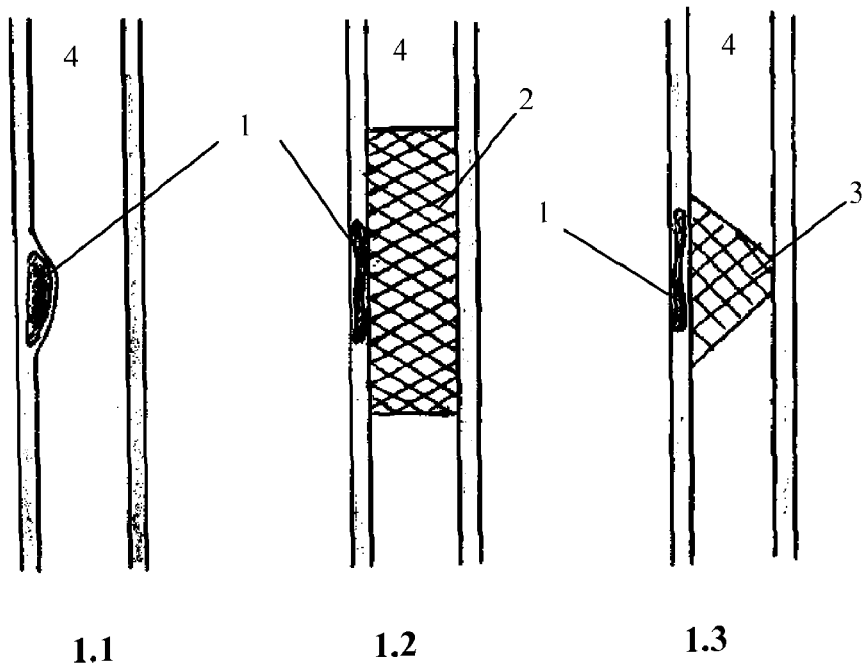
FIG. 1 shows a branchless blood vessel 4 with a bifurcation site 1 (view 1.1), and also some variants of stenting with the help of a traditional cylindrical stent 2 (view 1.2) and stenting with the truncated stent 3 (view 1.3) according to the invention. It is evident, that a traditional stent acts on (contacts with) much bigger area of a blood vessel walls, which results in higher degree of the wall trauma.
Figure 2:
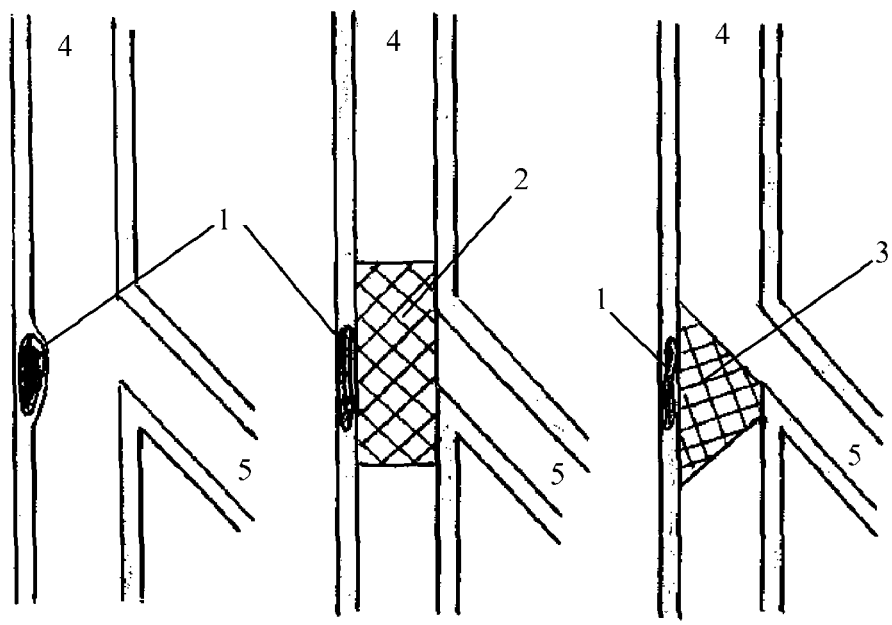
FIG. 2 shows a branched out blood vessel 4 with a bifurcation site (view 2.1), where 5 is a branch of the blood vessel 4, and some variants of stenting with a traditional stent 2 (view 2.2) and with a stent 3 formed according to the invention (view 2.3). It demonstrates the capability of stenting the main blood vessel without involving the mouth of the branch 5.
Figure 3:
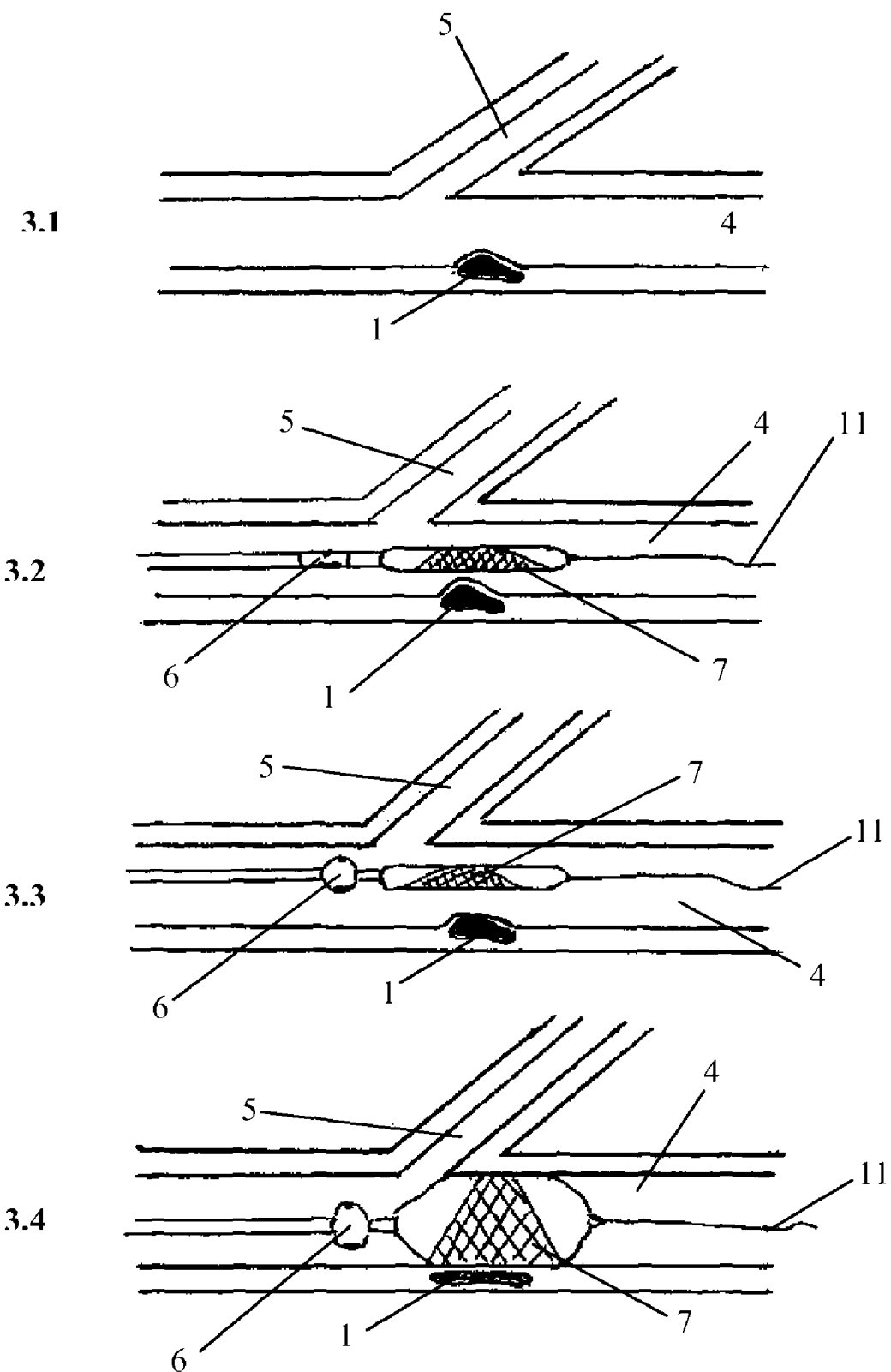
FIG. 3 illustrates the procedure of installing the stent in a blood vessel according to the invention, where 6 is the signal balloon, 7 is the basic balloon with mounted stent, 11 is the guiding conductor.
Figure 4:
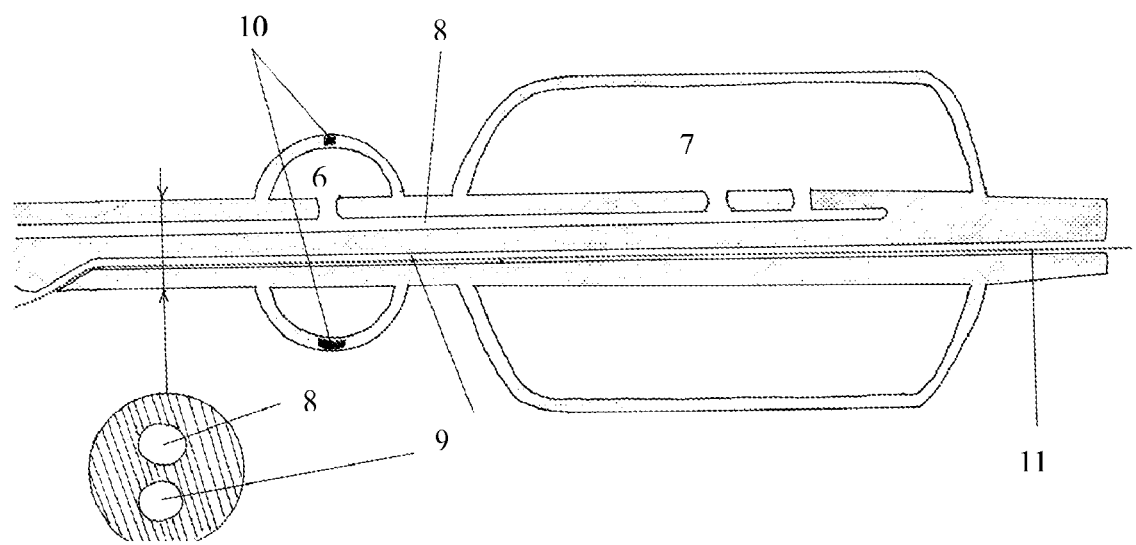
FIG. 4 shows a cross-section of two balloons which constitute the basis of the claimed delivery system, where 8 is the orifice of a polymeric catheter, 9 is the cross section of the multilumen part of the catheter, 11 is the guiding wire, 6 is the proximal (signal) balloon, 10 are the radiopaque labels (big and small markers), 7 is the distal balloon with a mounted stent.
Figure 5:
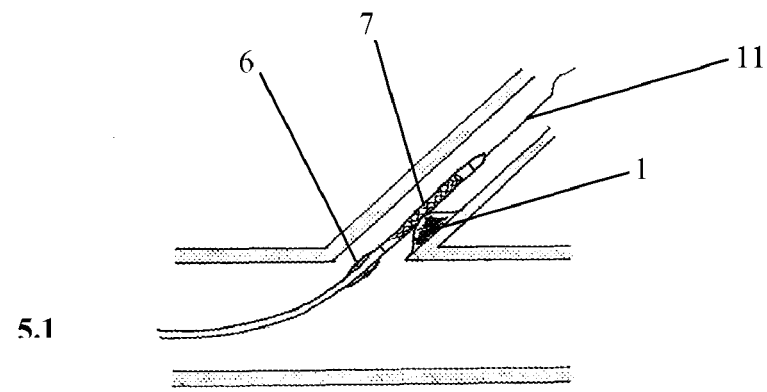
FIG. 5 illustrates the stages of high-precision delivery of the stent. The view 5.1 shows the bifurcation site of the branched out blood vessel and the eccentric stent 7 introduced in the branch by means of the two-balloon delivery system. The view 5.2 shows extension (dilation) of the proximal, i.e. the signal, balloon 6, which results in increase of the distance between the radiopaque labels (markers), thus enabling easy differentiation of their exact positions, for example, by the smaller label and, accordingly, the shorter side of the truncated stent. If necessary, the stent position is corrected by means of rotation and linear motion. As soon as the site of optimum location of the stent is registered, the pressure in the distal balloon is increased to provide expansion of the stent to the required size (view 5.3). Stent dimensions generally depend on the particular human arteries where it is intended to be used (e.g., peripheral or coronary arteries For example, for coronary arteries, stent diameter is about 1.5-6 mm, length about 8-40 mm; for carotid arteries, stent diameter is about 4-12 mm, length about 10-30 mm; for peripheral arteries, stent diameter 4-18 mm, length about 8-120 mm.
Figure 5:
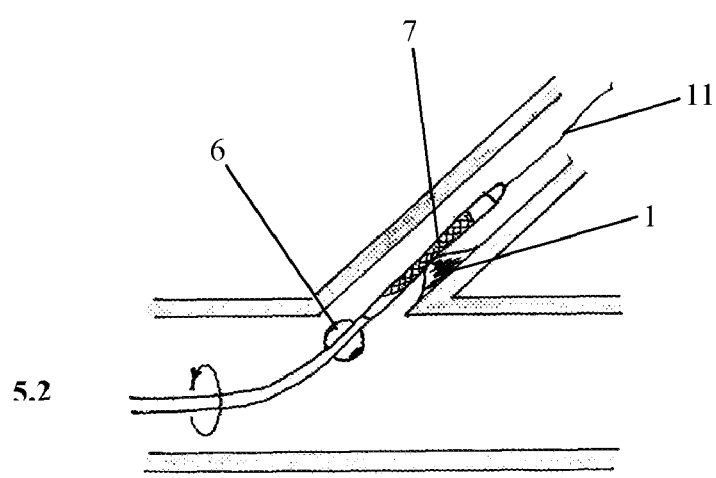
Figure 5:
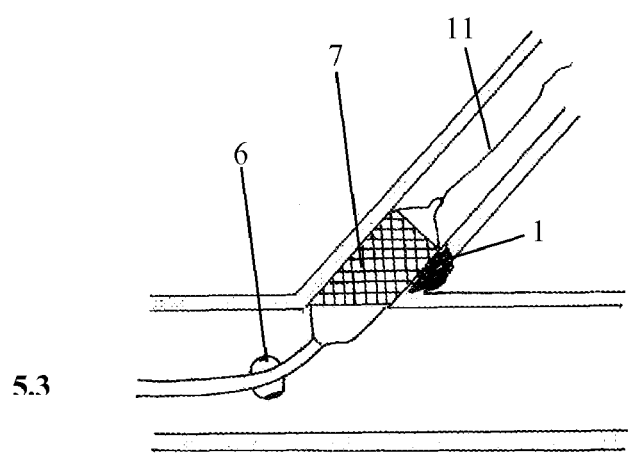

As can be seen from FIG. 5, creation of small pressure in the system of balloons, in the range of 1 to 2 atm., results, first of all, in expansion (dilation) of the "signal" balloon, because its expansion is not restricted mechanically by the mounted stent. This stage produces certain expansion (dilation) of the signal balloon, thereby moving apart the radiopaque labels to a distance that allows their easy visualization (differentiation). The smaller label, in this example, is located on the same line with the longer side of the truncated stent, the bigger label is located on the same line with the shorter side. Thus, by rotating delivery system about the axis it is possible to easily achieve the optimum position of the truncated stent in an artery. Further increase of pressure in the system of two balloons leads to expansion (dilation) of the distal balloon and the stent. Taking into consideration that the "signal" balloon has a smaller diameter than the basic balloon, the possibility of close traumatic contact with the arterial wall beyond the zone of stenting is excluded. Without the "signal" balloon it is practically impossible to determine, using the process of fluoroscopy, the spatial location of the sides of the truncated stent in a mounted state.

The proposed design of the double-balloon delivery system and the stent enables:

- precise implantation of an eccentric stent due to clear visualization of the radiopaque labels on the "signal" balloon, as each of these labels is located in the same plane either with the maximum or the minimum sides of the stent;
- optimizing the area of contact with the arterial wall in case of an eccentric unstable plaque, without traumatizing the neighboring clear zone of the wall;
- safe implantation of the eccentric stent in a zone of arterial bifurcation, without involving a orifice of a lateral arterial branch;
- optimal implantation of the stent into a orifice of a lateral branch without damaging a lumen of the main blood vessel.

The claimed delivery system can be used effectively for preventive stenting an unstable plaque, and also for routine stenting the bifurcation stenosis.

It should also be appreciated that various modifications, adaptations and alternative embodiments thereof may be made within the scope and spirit of the present invention. The invention is further defined by the following claims.

OTHER REFERENCES

Lefevre T. Et al., The Frontier stent registry: safety and feasibility of a novel dedicated stent for the treatment of bifurcation coronary artery lesions. J. Am. Coll. Cardiol. 2005; 46(4):592-8.

Thomas M. et al., Percutaneous coronary intervention for bifurcation disease. A consensus view from the first meeting of the European Bifurcation Club. EuroIntervention 2006; 2:149-153.

Laborde J C et al., Stentys coronary bifurcation stent. EuroIntervention 2007; 3:162-165.

Onuma Y., et al., Tryton I, First-In-Man (FIM) study: six month clinical and angiographic outcome, analysis with new quantitative coronary angiograph dedicated for bifurcation lesions. EuroIntervention 2008; 3:546-552.

Verheye S., Trauthen B., Axxess Biolimus A9 eluting bifurcation stentsystem. EuroIntervention 2007; 2:506-508.

What is claimed is:

1. A system for delivery of a stent expandable by a balloon, the system comprising:
   a multilumen polymeric catheter having at least two balloons at its input end, wherein the distal balloon is capable of expanding a stent mounted on it, the stent having at least one canted end,
   the proximal balloon having a smaller diameter than the distal balloon and having at least two radiopaque markers on its surface,
   the markers being of different size and used for rotational orientation of the stent,
   wherein the proximal balloon is capable of providing accurate rotational orientation of the stent in a side branch of an artery lumen.

2. The system of claim 1, wherein the stent is made of a material selected from the group consisting of 316L stainless steel, CoCr, CoNi, nitinol, platinum and gold.

3. The system of claim 1, wherein the stent is made of a biodegradable and biocompatible material.

4. The system of claim 1, wherein the stent is made of a biodegradable material with an embedded pharmaceutical or cell substance.

5. The system of claim 2, wherein the stent is covered by a pharmaceutical or cell substance.

6. The system of claim 2, wherein the stent is covered completely by a biodegradable polymer containing a pharmaceutical or cell substance.

7. The system of claim 2, wherein the stent is partially covered by a polymer containing a pharmaceutical substance.

8. The system of claim 2, wherein the stent is at least partially covered by a cell substance.

9. The system of claim 1, wherein both ends of the stent are canted such that a cylindrical surface of the stent is truncated at both ends, and an angle between the longitudinal axis of the stent and a truncating section plane is between 30 and 70 degrees.

10. The system of claim 1, wherein an angle between the longitudinal axis of the stent and a truncating section plane that forms the canted end is between 30 and 70 degrees.

11. The system of claim 1, wherein the proximal balloon has a smaller diameter and a shorter length, than the distal balloon.

12. The system of claim 11, wherein the bigger marker corresponds to a long side of the truncated stent, and the smaller marker corresponds to a short side of the truncated stent.

13. The system of claim 1, wherein the proximal balloon and the distal balloon are connected to a same lumen of the polymeric catheter.

14. The system of claim 1, wherein the proximal balloon and the distal balloon are connected to different lumens of the polymeric catheter.

* * * * *